(12) United States Patent
Gray et al.

(10) Patent No.: US 6,738,315 B1
(45) Date of Patent: May 18, 2004

(54) UNDERWATER TARGET TESTING

(75) Inventors: Harry P. Gray, McLean, VA (US); Brian S. Smale, New Carrollton, MD (US); Frederick A. Costanzo, Manassas, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/447,951

(22) Filed: May 30, 2003

(51) Int. Cl.[7] .................................................. G01M 7/00
(52) U.S. Cl. ......................... 367/145; 367/151; 367/13
(58) Field of Search ................................ 367/145, 151, 367/13, 173; 73/12.08; 181/116, 117, 118

(56) References Cited

U.S. PATENT DOCUMENTS 3,521,725 A * 7/1970 Petes et al. .................. 367/145
6,662,624 B1 * 12/2003 Thompson ................. 73/12.08

* cited by examiner

*Primary Examiner*—Daniel Pihulic
(74) *Attorney, Agent, or Firm*—Jacob Shuster

(57) ABSTRACT

An underwater target such as the hull of a ship is tested for its susceptibility to damage from explosive shock waves emerging from a rigid conical shell in response to detonation of an explosive charge therein. Such shell is located underwater in close spaced relation to the ship hull.

10 Claims, 2 Drawing Sheets

UNDERWATER TARGET TESTING

The present invention relates generally to underwater testing of targets, such as the hull of a ship, in regard to damage caused by shock waves produced by explosive detonation.

BACKGROUND OF THE INVENTION

At the present time, shock testing of ship hulls by the U.S. Navy is conducted by detonation of relatively large underwater explosive charges at a substantial distance from the ship. In order to insure safety and minimize detrimental environmental effects resulting from such testing, expensive measures are taken that substantially increase the costs of such testing, involving time consuming assembly of costly parts. It is therefore an important object of the present invention to provide such shock wave testing involving detonation of an explosive charge underwater, that is substantially less costly and more quickly and easily performed.

SUMMARY OF THE INVENTION

In accordance with present invention, shock wave testing is performed by positioning a substantially small explosive charge relatively close to an underwater target and within an underwater shell enclosure having an open end from which focused shock waves emerge in a direction onto the target. The enclosure shell is conical shaped having a rigid inner liner externally covered by foam so as to focus shock waves produced by detonation onto the target such as a ship hull from the close location at sea or within a harbor, and by use of small quantities of explosive charge.

BRIEF DESCRIPTION OF DRAWING FIGURES

A more complete appreciation of the invention and many of its attendant advantages will he readily appreciated as the same becomes better understood by reference to the following detailed description when considered in connection with the accompanying drawing wherein.

DETAILED DESCRIPTION OF PREFERRED EMBODIMENT

Figure 1:
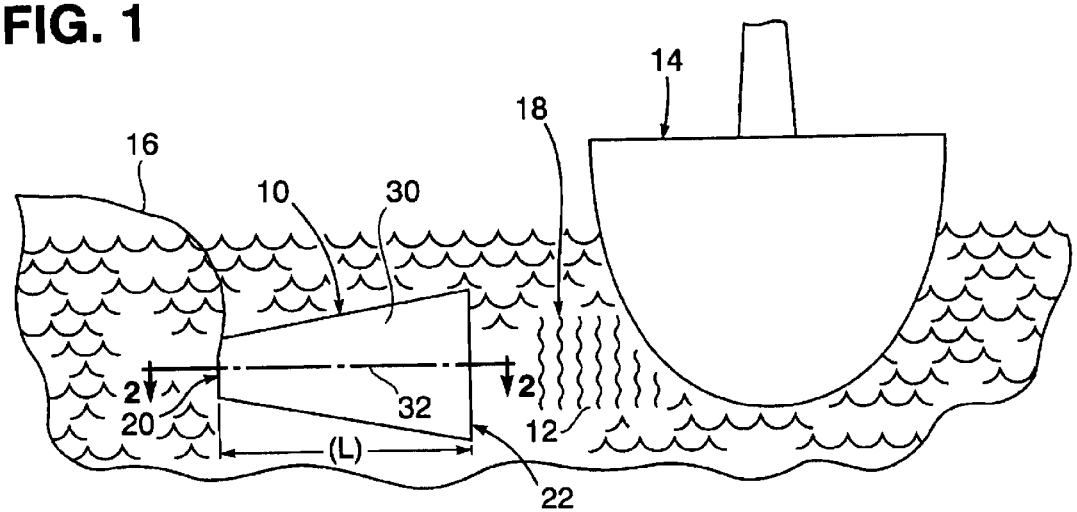
FIG. 1 is a simplified side elevation view illustration of an underwater submerged shock wave testing facility located relatively close to a target, such as the hull of a ship.

Referring now to the drawing in detail, FIG. 1 shows a testing device 10, constructed in accordance with the present invention, located underwater within a body of seawater 12, closely spaced from a target such as a ship hull 14. The testing device 10 is connected by wiring 16 for example, to some control facility (not shown) so as to detonate an explosive charge within the testing device 10 and thereby produce shock waves 18 focused onto the target 14.

Figure 2:
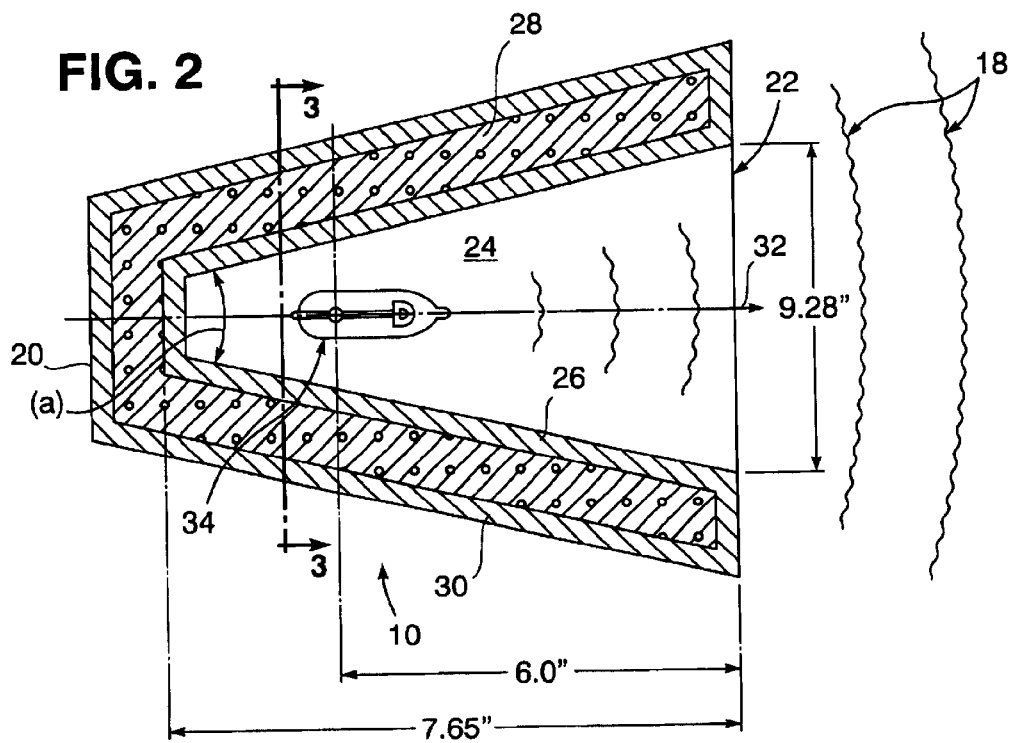
FIG. 2 is a top section view taken substantially through a plane indicated by section line 2—2 in FIG. 1.
Figure 3:
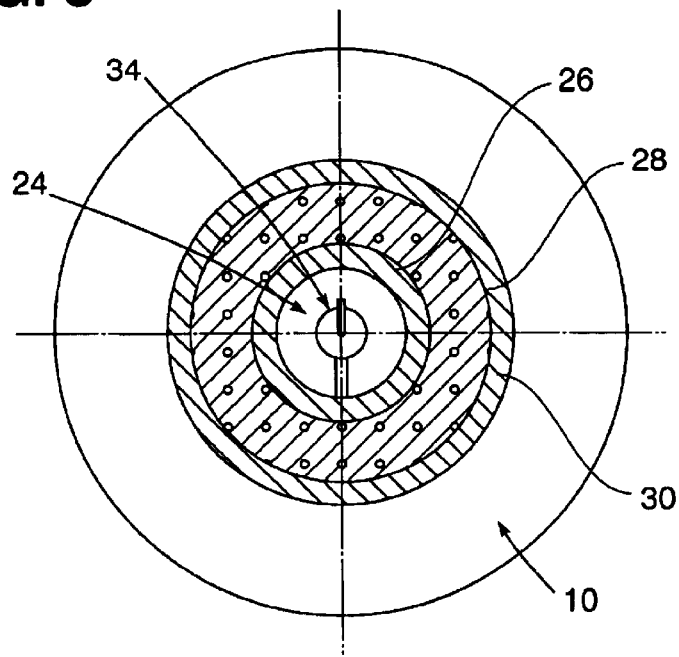
FIG. 3 is a section view taken substantially through a plane indicated by section line 3—3 in FIG. 2.

Referring now to FIGS. 2 and 3, the testing device 10 has a relatively small closed end 20 and a substantially large open end 22 from which the shock waves 18 emerge. Internally, the testing device 10 has a waterproof chamber 24 enclosed within a rigid metallic liner 26 made of steel for example. A layer of foam 28 covers the liner 26 throughout, enclosed within an outer metallic casing 30 which is much thinner than the inner liner 26 and may also be made of steel. The chamber 24 is conical shaped with an axis 32 aligned with a targeting path for the shock waves 18, which are generated by detonation of an explosive charge 34 positioned within the chamber 24 on its axis 32.

As shown in FIGS. 1 and 2, the side walls formed by the liner 26 extend from the closed end 20 at an apex angle alpha ($\alpha$) to form the conical shaped chamber 24 having an axial length (L) from the open end 22 to the closed end 20. The explosive charge 34 is supported in the chamber 24 along its axis 32 as shown in FIG. 3.

As a result of the foregoing arrangement associated with the targeting device 10, shock waves generated by detonation of the explosive charge 34 are focused along the axis 32 when emerging from the open end 22 of the chamber 24. The magnitude and shape of such shock waves 18 is determined by the weight of the charge 34, the apex angle ($\alpha$) between the side walls of the liner 26, the length (L) of the device 10 and the thickness of the liner 26. Accordingly, the energy of the resulting focused shock waves 18 may be made relatively large despite the relatively small quantity of explosive charge utilized.

As indicated in FIG. 2, pursuant to successful tests performed, establishing the latter referred to beneficial attributes of the present invention, by way of example the axial length (L) of the chamber 24 was 7.65 inches, smaller than the width at the open end 22 of 9.28 inches. The explosive charge 34 was then located 6.0 inches from the open end 22 along the axis 32.

Figure 4:
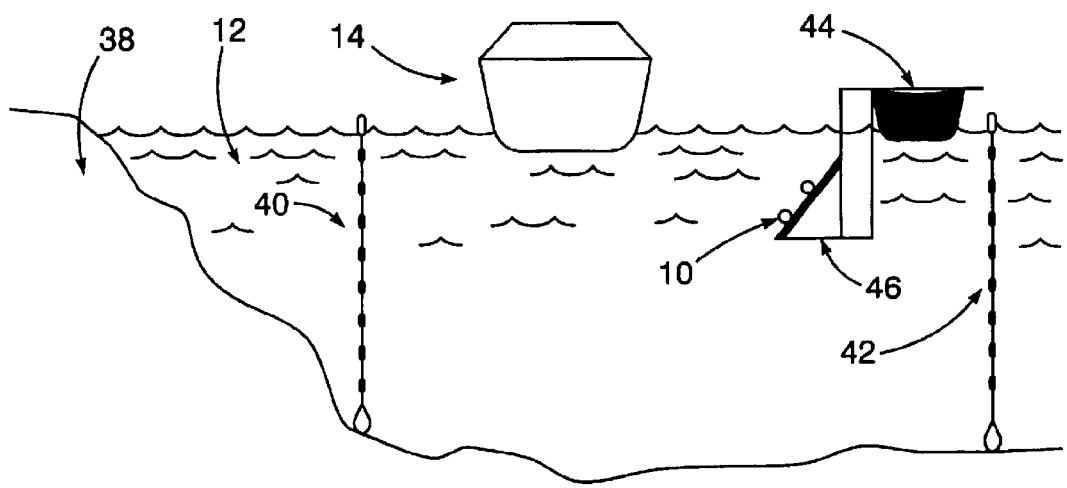
FIG. 4 is a simplified side elevation view illustration of an embodiment of the invention involving shock wave testing.

Referring now to FIG. 4, an embodiment of the present invention as hereinbefore described is shown within a harbor, wherein the ship hull target 14 is in relatively close spaced relation to a shore 38 from which the seawater 12 extends. The harbor location for the ship hull target 14 is defined between nettings 40 and 42, with a testing barge 44 positioned adjacent to the netting 42. An array of testing devices 10 as hereinbefore described, are connected by wiring to control facilities on the barge 44 and supported by the barge 44 in focused positions relative to the ship hull target 14 by means of a positioning facility 46. Such use of the present invention at the harbor location as diagrammed in FIG. 4 for shock wave testing purposes will eliminate logistic cost associated with at sea testing locations remote from the seashore 38.

Obviously, other modifications and variations of the present invention may be possible in light of the foregoing teachings. It is therefore to be understood that within the scope of the appended claims the invention may be practiced otherwise than as specifically described.

What is claimed is:

1. An underwater testing device, comprising: a waterproof enclosure having a rigid liner with an outlet; explosive charge means insertable into the enclosure for detonation therein to produce shock waves; and layer means on the liner for focusing said shock waves within the enclosure along a targeting direction through the outlet.

2. The testing device as defined in claim 1, wherein the liner is a metallic shell and the layer means is foam enclosed within a metallic casing.

3. The testing device as defined in claim 2, wherein the liner is conical shaped and extends between a closed end of the enclosure and an open end through which said targeting direction extends.

4. The testing device as defined in claim 1, wherein the liner is conical shaped and extends between a closed end of the enclosure and an open end through which said targeting direction extends.

5. A method of testing an underwater target subject to damage by shock waves, comprising the steps of: inserting an explosive charge into a shell that is rigid throughout; positioning the shell with the charge therein underwater adjacent to and in directional alignment with an underwater target; and detonating the charge to produce shock waves emitted from the shell for application to the target.

6. The method as defined in claim 5, wherein the shock waves are enhanced by focusing within the shell.

7. The method as defined in claim 6, wherein the target is a ship hull to which the shock waves are applied underwater.

8. The method as defined in claim 7, wherein the target is located within seawater at a harbor location.

9. The method as defined in claim 5, wherein the underwater target is a ship hull located within seawater at a harbor location.

10. The method as defined in claim 9, wherein the shell is positioned by a barge in the harbor location to control detonation of the charge in the shell and directionally focus the shock waves emitted therefrom onto the ship hull target.

* * * * *